US006649610B1

(12) United States Patent
Miles et al.

(10) Patent No.: US 6,649,610 B1

(45) Date of Patent: Nov. 18, 2003

(54) 2-OXO-1, 4-BENZOXAZINE COMPOUNDS FOR TREATMENT OF TUBERCULOSIS

(75) Inventors: D. Howard Miles, Winter Springs, FL (US); Krasnykh Olga Petrovna, Perm (RU); Saleh Naser, Orlando, FL (US); Solodnikov Sergey Yurjevich, Perm (RU); Elena A. Goun, Stanford, CA (US); Suslonov Vladimir Michailovich, Perm (RU)

(73) Assignee: University of Central Florida, Orlando, FL (US)

( * ) Notice: Subject to any disclaimer, the term of this patent is extended or adjusted under 35 U.S.C. 154(b) by 0 days.

(21) Appl. No.: 10/153,111

(22) Filed: May 22, 2002

Related U.S. Application Data

(60) Provisional application No. 60/292,985, filed on May 23, 2001.

(51) Int. Cl.[7] .................... A61K 31/535; C07D 265/36; C07D 498/02

(52) U.S. Cl. .................................... 514/230.5; 544/105

(58) Field of Search ........................ 544/105; 514/230.5

(56) References Cited

U.S. PATENT DOCUMENTS

| | | | | |
|---|---|---|---|---|
| 5,274,002 | A | 12/1993 | Hawkins | 514/530 |
| 5,334,612 | A | 8/1994 | Kalden et al. | 514/440 |
| 5,972,363 | A | 10/1999 | Clikeman et al. | 424/408 |
| 6,066,670 | A | 5/2000 | Brown | 514/557 |
| 6,080,790 | A | 6/2000 | Boyd et al. | 514/650 |

*Primary Examiner*—Bruck Kifle

(74) *Attorney, Agent, or Firm*—Brian S. Steinberger; Law Offices of Brian S. Steinberger, P.A.

(57) ABSTRACT

Compounds belonging to novel classes of 2-oxo-1,4-benzoxazine heterocyclic compounds and their close derivatives, are disclosed along with the surprising use property of these compounds as bacteriostatic agents for humans and non-humans against mycobacteria. These species include: 4-benzoyl-3-benzoyloxy-2-(2-oxo-2H-1,4-benzoxazin-3-yl)pyrido[2,1-c][1,4]benzoxazin-1,5-dione; and, 2,4,6-trimethylphenyl 2-(3,4-dihydro-2-oxo-2H-1,4-benzoxazin-3-ylidene)-3-p-methoxyphenyl-3-oxo-propanoate.

7 Claims, 1 Drawing Sheet

2-OXO-1, 4-BENZOXAZINE COMPOUNDS FOR TREATMENT OF TUBERCULOSIS

This application claims the benefit of priority of U.S. Provisional Application Serial No. 60/292,985 filed May 23, 2001.

FIELD OF THE INVENTION

This invention relates to novel 2-oxo-1,4-benzoxazine heterocyclics and more particularly to certain novel compounds and their close derivatives and to the use of these compounds as a bacteriostatic agent (a chemical agent that stops or inhibits the multiplication of bacteria) for human and non-humans against *Mycobacterium tuberculosis.*

BACKGROUND OF THE INVENTION

The infectious disease, tuberculosis (TB), is the leading cause of death worldwide from a single human pathogen, claiming more adult lives than diseases such as acquired immunodeficiency syndrome (AIDS), malaria, diarrhea, leprosy and all other tropical diseases combined (Zumla A, Grange J. B M J (1998) 316, 1962–1964). The organism usually responsible is the tubercle bacillus, *Mycobacterium tuberculosis* (MT), discovered by Robert Koch in 1882. However, *M. bovis*, which infects cattle may also infect man and *M. africanum* is a cause of TB in West Africa. Furthermore, a number of normally non-pathogenic mycobacteria, especially *M. avium, M. intracellulare* and *M. scrofulaceum*, cause opportunistic infectious disease in patients with AIDS (Horne N. 1996. Tuberculosis and other mycobacteria diseases. In Mansons Tropical Diseases, $20^{th}$ edn, Cook FEG (ed). W B Saunders: London; 971–1015). Pulmonary TB, the most common type of the disease, is usually acquired by inhalation of the bacillus from an infectious patient and causes irreversible lung destruction.

About one third of the world's population is currently infected with *M. tuberculosis*; 10% of those infected will develop clinical diseases, particularly those who also have the human immunodeficiency virus (HIV) infection (Zumla A, Grange J. B M J (1998) 316, 1962–1964). With the discovery of effective anti-mycobacterial agents (including ethambutol, isoniazid, pyrazinamide, rifampicin and streptomycin) and a reduction in poverty, there was a drastic decline in the number of TB cases, especially in developed nations. However, since the late 1980s, the number of cases of TB throughout the world has been increasing rapidly partly due to the emergence of multi-drug resistant *M. tuberculosis* (C. E. Barry, III, Biochemical Pharmacology (1997) 54, 1165–1172). According to the World Health Organization (World Health Organization. 1993 92. per Besra G S, Brennan P J. 1997. J Pharm Pharmacol 49 (Suppl. 1):25–30.s), it is expected that the annual death rate caused by TB will reach an overwhelming 3.5 million by the year 2000.

Thus the TB problem requires urgent attention. Short course anti-TB regiments initially using at least three first-line drugs (including isoniazid, rifampicin and pyrazinamide) are often not effective due to an increase in the number of tuberculosis strains that have become resistant to current drugs. For example the World Health Organization (WHO) recently reported that the death rate of patients with multi-drug resistant (MDR) tuberculosis in the US was approximately 70%. Current treatment is also very expensive: a 3 drugs regimen is needed (more than $500/month cost per patient). Thus the major problems faced in tuberculosis control are poor infrastructures for diagnosis and drug supply. The failure of patients to complete therapy as well as inappropriate monotherapy has led to the emergence and distribution of strains of *Mycobacterium tuberculosis* resistant to every available chemotherapy (Bloom B R and Murray C J L, Science (1992) 257, 1055–1064). Such organisms will not remain confined to the Third World or to the poor and indigent of developed countries. The recent documentation of the spread of a single clone of multi-drug-resistant *Mycobacterium tuberculosis* (the "W" strain) throughout the continental United States and Europe highlights the danger of an airborne pathogen in our global society (Bifani P J, et al., JAMA (1996) 275, 452–457).

The patent literature has numerous accounts of benzoxazine heterocyclics including:

Frechette (U.S. Pat. No. 5,696,117), Frechette (U.S. Pat. No. 5,854,242) and Frechette (U.S. Pat. No. 5,707,990) describe 148 benzoxazine and pyrido-oxazine heterocyyclic as anti-bacterial compounds;

Omedi-Sale (U.S. Pat. No. 3,862,954) shows tri-azole compounds for CNS use;

Hawkins (U.S. Pat. No. 5,274,002) describes many analogs of phenyl ethers of a substituted phenyl of the formula structure at column 1, lines 49–60 with 37 examples of specific compounds which compounds may be useful for tumor inhibition (column 22, line 64); and, Boyd, et al (U.S. Pat. No. 6,080,790) also describes many tri-substituted phenyl derivatives according to the formula of the Abstract with 15 examples of specific compounds which may be useful for malignant skin diseases (column 5, line 46).

For half a century, the most used antimicrobial agents referenced above for prophylaxis and treatment of tuberculosis since 1952 is isoniazid (isonicotinic acid hydrazide [INH]). One of the known complications of anti-tuberculosis chemotherapy caused by this drug is liver dysfunction plus a great number of other complications. The toxicity of INH is also a serious problem frequently resulting in poisoning. It is also known to be an acute/chronic hazards since INH is an irritant of the skin, eyes, mucous membranes and upper respiratory tract.

It appears from a review of the above that the benzoxazine heterocyclic compounds of interest are not disclosed nor is there any report of activity against *Mycobacterium tuberculosis* or related mycobacteria.

Consequently, there is a need for an anti-mycobacteria drug for humans and non-humans which mitigates the above mentioned disadvantages of current drug bacteriostatic agent effectiveness against human and non-human mycobacteria.

SUMMARY OF THE INVENTION

The first objective of the present invention is to provide a bacteriostatic agent this is effective against mycobacteria.

The second object of this invention is to provide a bacteriostatic agent that is effective in human and non-humans against mycobacteria.

A third object of this invention is to provide a bacteriostatic agent that is effective in human and non-humans against *Mycobacterium tuberculosis.*

A further object of this invention is to provide novel 2-oxo-1,4-benzoxazine heterocyclics.

A preferred embodiment of the invention encompasses a class of heterocyclics having the property of bacteriostatic agent activity against *Mycobacterium tuberculosis* comprising 2-oxo-1,4-benzoxazine heterocyclics and more specifically those heterocyclics: 4-benzoyl-3-benzoyloxy-2-(2-oxo-2H-1,4-benzoxazin-3-yl)pyrido[2,1-c][1,4]benzoxazin-1,5-dione; and, 2,4,6-trimethylphenyl 2-(3,4-dihydro-2-oxo-2H-1,4-benzoxazin-3-ylidene)-3-p-methoxyphenyl-3-oxo-propanoate and the use of each in human and non-humans as therapeutic means for the eradication of *Mycobacterium tuberculosis*.

Further objects and advantages of this invention will be apparent from the following detailed description of presently preferred embodiments which are illustrated structurally in the accompanying drawings.

DESCRIPTION OF THE PREFERRED EMBODIMENTS

Before explaining the disclosed embodiments of the present invention in detail, it is to be understood that the invention is not limited in its application to the details of the particular arrangement shown since the invention is capable of other embodiments. Also, the terminology used herein is for the purpose of description and not of limitation.

The general class of 2-oxo-1,4-benzoxazine heterocyclics is more fully illustrated by those compounds having the structure:

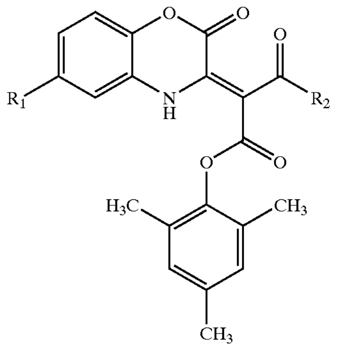

$R_1$=H or $CH_3$ $R_2$=aryl

Figure 1:
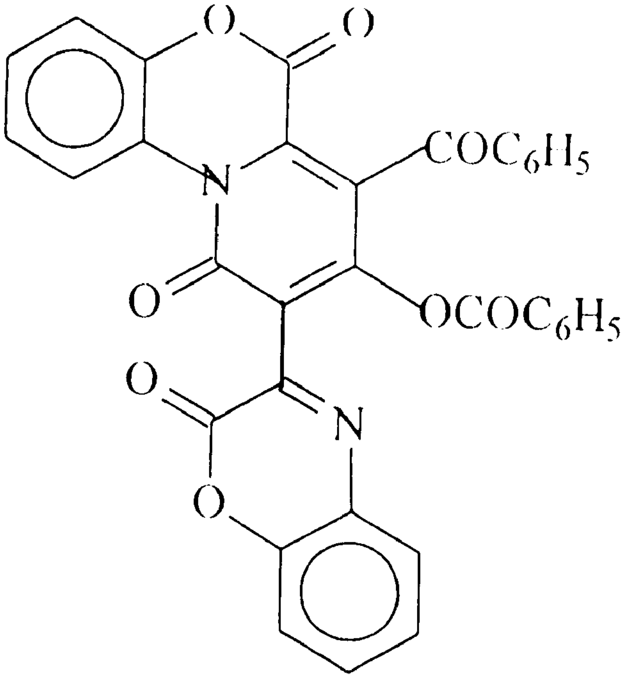
FIG. 1 illustrates structurally a chemical compound designated as 1F-18.
Figure 2:
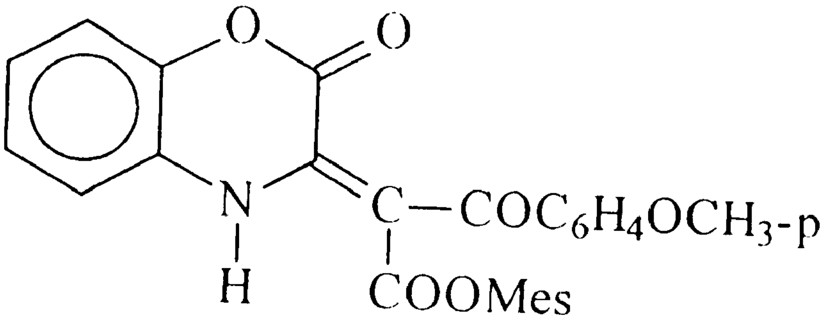
FIG. 2 illustrates structurally a chemical compound designated as 1F-19.

More specifically this application is for the anti-tuberculosis compounds 1F-18 and 1F-19, which have been structurally shown in FIGS. 1 and 2, respectively. Compound 1F-18 surprisingly has also demonstrated 100% activity against human and non-human myeloma.

To facilitate a full understanding of the invention: the compound designated as 1F-18 is 4-benzoyl-3-benzoyloxy-2-(2-oxo-2H-1,4-benzoxazin-3-yl)pyrido[2,1-c][1,4]benzoxazin-1,5-dione; and, the compound designated as 1F-19 is 2,4,6-trimethylphenyl 2-(3,4-dihydro-2-oxo-2H-1,4-benzoxazin-3-ylidene)-3-p-methoxyphenyl-3-oxo-propanoate.

These compounds are highly active against *Mycobacterium tuberculosis* and have a very low toxicity, a lethal dose 50 ($LD_{50}$) in animals. The percent activity and animal toxicity for each compound is as follows: 1F-18 (95% and $LD_{50}$>2000 mg/kg), and 1F-19 (97% and $LD_{50}$>1000 mg/kg).

Solubility: highly soluble in DMSO, DMFA, dichloroethane, acetonitrile; somewhat soluble in ethanol, tetrachloromethane; and, insoluble in hexane and water.

PREPARATION OF 1F-18

EXAMPLE 1

The preparation of 4-benzoyl-3-benzoyloxy-2-(2-oxo-2H-1,4-benzoxazin-3-yl)pyrido[2,1-c][1,4]benzoxazin-1,5-dione (1F-18).

A solution of 1.5 g (0.047 moles) of compound 4 in 10 mL of dowtherm A ** was kept at constant temperature at 183–186° C. for 30 min. The solution was cooled and the resulting precipitate of 1F-18 was filtered and recrystallized from acetonitrile to give 0.79 g (54%) of orange crystals with mp of 259–261° C. (decomposes).

The following reactions are illustrative of the synthesis of (1F-18)

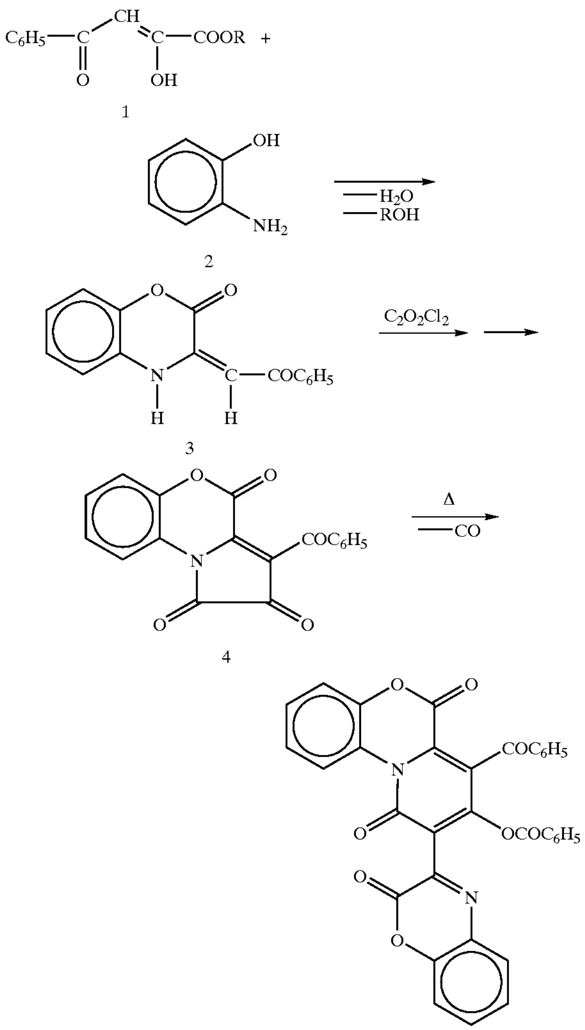

1

2

3

4

1F-18

R = H or Alk($CH_3$, $C_2H_5$)

**Content: 73.5% phenyl ether
26.5% diphenyl

Described in L. Fieser, M. Fieser, Reagents for Organic Synthesis, Wiley, New York, 1968.

A detailed synthesis of compound 4 has been published earlier in: Five-membered-ring 2,3-dioxoheterocycles.

XXXIII. Synthesis of 3-aroyl-1,2-dihydro-4H-pyrrolo[5,1-c][1,4]benzoxazine-1,2,4-triones and their reaction with water and alcohols. Mashivets, A. N.; Mashevskaya, I. V.; Krasnykh, O. P.; Shurov, S. N.; Andreichikov, V. S. Perm. Gos. Univ., Perm, Russia. Zh. Org. Khim. (1992), 28(12), 2545–53. CODEN: ZORKAE ISSN: 0514-7492 and the synthesis of compound 3 was previously published by Iwanami Y., Seki T., Inagaki T., Bull. Chem. Soc. Jpn., 1971, 44, 1316. and Iwanami Y., Inagaki T., J. Heterocycl. Chem., 1976, 13(4), 681–684.

PREPARATION OF 1F-19

EXAMPLE 2

The preparation of 2,4,6-trimethylphenyl 2-(3,4-dihydro-2-oxo-2H-1,4-benzoxazin-3-ylidene)-3-p-methoxyphenyl-3-oxo-propanoate (1F-19). A solution of 0.5 g (0.0014 moles) of compound 4' and 0.38 g (0.0028 moles) of 2,4,6-trimethylphenol in 10 ml of absolute pseudocumene was refluxed for 20 min, cooled and the resulting precipitate of 1F-19 was filtered and recrystallized from phenol to give 0.52 g (80%) of yellow crystals with mp of 224–227° C.

Solubility: The compound is highly soluble in in DMSO, DMFA, acetonitrile, dichloroethane; somewhat soluble in phenol, tetrachloromethane; and, insoluble in hexane and water.

The following reactions are illustrative of the synthesis of (1F-19)

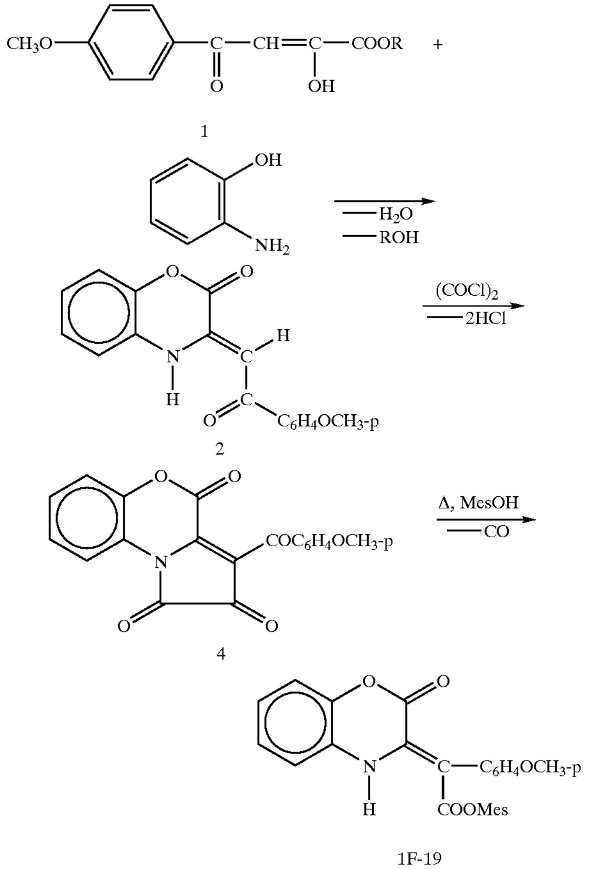

1

2

4

1F-19

A

-continued

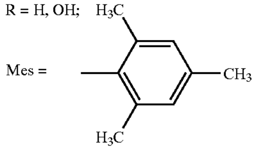

In polar solutions of 1F-19 the presence of small amounts of tautomer is observed.

The bacteriostatic activity against *Mycobacterium tuberculosis* of the novel compounds (as earlier reported on page 5, lines 9–12) was realized by the following procedure.

BIO-ASSAY PROCEDURE

Compound processing: Synthetic compounds 1F-18, and 1F-19 were each first dissolved in 500 ml of dimethylsulfoxide (DMSO) in individual beakers and each placed on a rotary shaker overnight. Distilled water was added to each to provide a final concentration of 10 mg/ml. Each solution was filter-sterilized using Becton Dickinson 5 ml sterile syringes and Whatman 22 um sterile filters. Each of the filtered sterilized synthetic test solutions (designated as synthons hereafter) were stored at −20 degrees centigrade until used.

Culture media and bioassay analytical techniques: BACTEC 12B Mycobacteria also known as Middlebrook 7H12 Medium was purchased from Becton Dickinson (Pittsburgh, Pa.). It contains 7H9 broth base, casein hydrolysate, bovine serum albumin, catalase and palmitic acid labeled with $^{14}C$. It is specific for growing Mycobacteria and is used in conjunction with the BACTEC brand 460 TB Analyzer. This Middlebrook 7H9 broth base media consist of 4 ml of broth mixture included in a sealed bottle. The culture used in the bioassay was *M. tuberculosis* ATCC 25177. The synthons were added to Bactec 7H12 B+ bottled liquid media using Becton Dickinson B-D 1 ml sterile syringes to a final concentration of 0.1 mg/ml. To each of these Bactec bottles, 100 ul of Bactec 7H12 B+ cultured *M. tuberculosis* was inoculated using Becton Dickinson B-D "1 cc" sterile syringes. Microbial growth activity in this culture medium is indicated by the release of $^{14}CO_2$ into the atmosphere of the sealed vial following the hydrolysis of $^{14}C$-labeled palmitic acid by the microorganism. The BACTEC 460 TB Analyzer: The gas in the atmosphere of the sealed BACTEC 12B vial is aspirated from the vial via a sterile needle attached to a robotic inside the BACTEC 460 TB Analyzer System. The BACTEC Analyzer operates by initially drawing room air through a dust filter, a flush valve, and an ion chamber transferring all $^{14}CO_2$ into $CO_2$ trap where it is retained. This process cleans the electrometer and leaves it ready to start the next cycle. During the next cycle, a pair of 18G needles are heated. A pump produces a partial vacuum in the ion chamber used to lower the testing needles through the rubber septum of the vial being tested. A vacuum draws culture gas from the vial to the ion chamber. The electrometer measures the very small current that the radioactive $^{14}CO_2$ produces in the ion chamber. Following removal of the radioactive culture gas, fresh 5% $CO_2$ is introduced into the medium headspace every time a vial is tested, enhancing the growth of mycobacteria. The current measured by the electrometer is amplified and displayed as a growth index (GI). The growth index is measured on a scale of 0 to 999 and is an indication of microbial growth activity in the bottle. Usually, a GI of 10 or higher is an indication of definite microbial growth. The percent growth, and the percent inhibition in the presence of extract was calculated by the following formulas:

$$\%GR = \frac{GI(\text{with no extract})}{GI(\text{with the extract})} \times 100\%$$

*GR*:Percent growth, *GI*:Growth index, *IN*:Percent inhibition

Animal Toxicity Bioassay. Acute toxicity was studied on white mice of both sexes with weight ranging between 18–26 grams under intraperitoneal injection of 2% solution of tested compound in starch (the compound was dissolved in starch slime and injected) on the basis of 0.1 ml of solution per 10 g of the animal weight. Each dose was tested on the group of 6 animals that were observed during 14 day period. (This method was approved by the Pharmacology committee of Russian Ministry of Health and has been widely used since 1968.) Averaged lethal dose ($LD_{50}$) of the compound was computed using results of experiments on 5–7 groups of animals using the method of Litchfield and Wilkinson. (Belenkii M. L. “Elements of quantative determination of the pharmacological effect,” Leningrad, 1963, 71 pages).

The disclosed invention makes it possible to produce and isolate oxo-heterocyclics, which have the property of bacteriostatic agent activity toward *Mycobacterium tuberculosis.*

ADVANTAGES OF THE DISCOVERY

This discovery has several advantages. In the Background of the Invention there was a short description of one of the most used primary anti-mycobacteria agents for prophylaxis and treatment of tuberculosis since 1952. The name of this drug is isoniazid (isonicotinic acid hydrazide [INH]). Patients with a recently positive protein positive derivative (PPD) skin test and a normal chest x-ray routinely are given a 6- to 9-month course of isoniazid. Liver dysfunction is one of known complications of anti-tuberculosis chemotherapy caused by this drug among a great number of other complications when isoniazid is co-administrated with other drugs (W. W. Yew, Clinica Chimica Acta 313 (2001) 31–36).

The toxicity issue is also a serious problem. In the US: A surveillance of cases of isoniazid poisoning by the American Association of Poison Control Centers from 1985–1993 revealed a low number of 138 cases in 1985, with no fatalities, and a high number of 2656 cases in 1991, with 6 fatalities. Mortality/Morbidity: Acute ingestion by adults with as little as 1.5 g of isoniazid can lead to mild toxicity. Ingestion of 6–10 g may be fatal, while ingestion of 15 g is usually fatal if not appropriately treated. The overall mortality rate for acute isoniazid toxicity has been estimated to be 19%. With current methods of supportive care, however, this figure may be high. From 1972–1988, an estimated 152 fatalities were caused by isoniazid-related hepatitis. The overall hepatitis-related death rates among patients using isoniazid prophylaxis is approximately 0.001%. Among individuals who complete a full course of prophylaxis, the hepatitis-related death rate has been calculated to be 23.2–57.9/100,000. The mortality rate among individuals who develop overt isoniazid-induced hepatitis is 10%.

Isoniazid is also known to be anacute/chronic hazards. This compound is an irritant of the skin, eyes, mucous membranes and upper respiratory tract. It can cause harm by ingestion, inhalation and skin absorption [Lenga, Robert E. The Sigma-Aldrich Library of Chemical Safety Data. Edition 1. Sigma-Aldrich Corporation. Milwaukee, Wis. 1985. p. 1114, #A.].

The acute toxicity of isoniazid is as following: LCL0 (lowest published lethal concentration) for man is 100 mg/kg. In animal testing with white mouse $LD_{50}$ (lethal dose 50 percent kill) for isoniazid was shown to be 100 mg/kg (the same intraperitoneal injection method (Krasil'nikov, I. I.; Parfenov, A. I.; Strel'nikov, Yu. E.; Smirnova, S. M. Radiobiologiya (1973), 13(4), 551-4), which was used by us to determine $LD_{50}$ dose). All toxicity information about isoniazid can also be found on the web site: http://ntp-server.niehs.nih.gov/htdocs/Chem H&S/NTP Chem5/Radian54-85-3.html In addition there are a number of reports in recent literature which suggest the importance of developing a new treatment to combat strains of the deadly disease, tuberculosis, which have become resistant to current drugs.

By reference to page 5, lines 9–12 it is seen that all of the specific compounds of the invention exhibit at least 10 times lower acute toxicity compare to isoniazid and high activity values.

The heterocyclic 2-oxo-1,4-benzoxazine compounds of the invention which are unique in their anti-tubercular activity are to be used in a pharmaceutical composition comprising a non-toxic effective amount of the referenced heterocyclic compound or a tautomeric form thereof or a pharmaceutically acceptable salt thereof or pharmaceutically acceptable solvate thereof, and a pharmaceutically acceptable carrier therefor.

Additional derivatives of the heterocylic 2-oxo-1,4 benzoxazine compounds are hereafter set forth in the following table which derivatives conform to the structural formula indicated by:

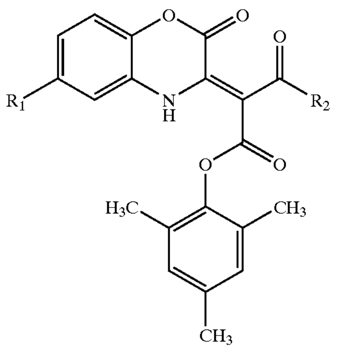

$R_1$=H or $CH_3$ $R_2$=aryl

| # | Structure | Name |
|---|---|---|
| 1 | 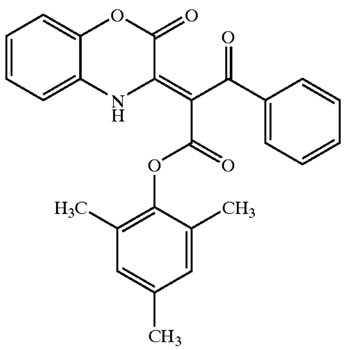 | 3-Oxo-2-(2-oxo-4H-benzo[1,4]oxazin-3-ylidene)-3-phenyl-propionic acid 2,4,6-trimethyl-phenyl ester |
| 2 | 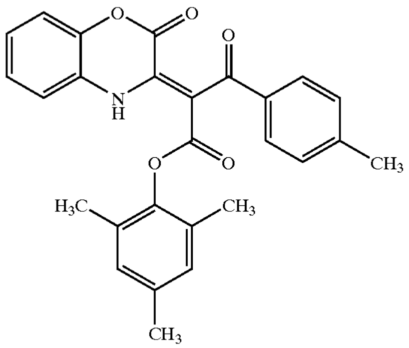 | 3-Oxo-2-(2-oxo-4H-benzo[1,4]oxazin-3-ylidene)-3-p-tolyl-propionic acid 2,4,6-trimethyl-phenyl ester |
| 3 | 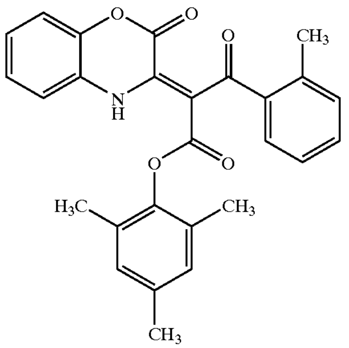 | 3-Oxo-2-(2-oxo-4H-benzo[1,4]oxazin-3-ylidene)-3-o-tolyl-propionic acid 2,4,6-trimethyl-phenyl ester |
| 4 | 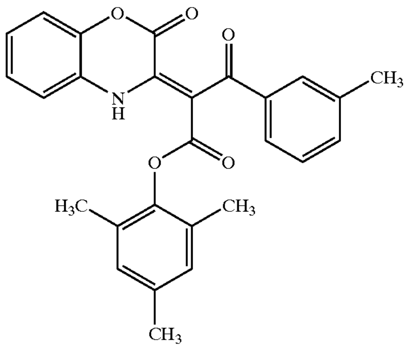 | 3-Oxo-2-(2-oxo-4H-benzo[1,4]oxazin-3-ylidene)-3-m-tolyl-propionic acid 2,4,6-trimethyl-phenyl ester |

-continued

| # | Structure | Name |
|---|---|---|
| 5 | 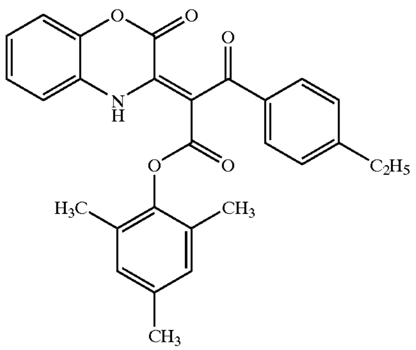 | 3-(4-Ethyl-phenyl)-3-oxo-2-(2-oxo-4H-benzo[1,4]oxazin-3-ylidene)-propionic acid 2,4,6-trimethyl-phenyl ester |
| 6 | 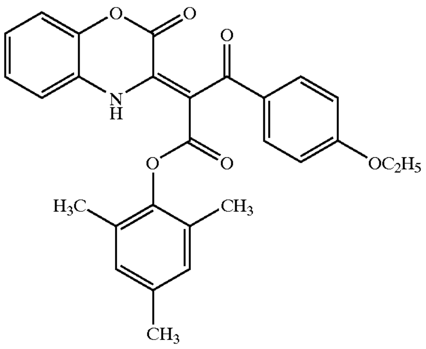 | 3-(4-Ethoxy-phenyl)-3-oxo-2-(2-oxo-4H-benzo[1,4]oxazin-3-ylidene)-propionic acid 2,4,6-trimethyl-phenyl ester |
| 7 | 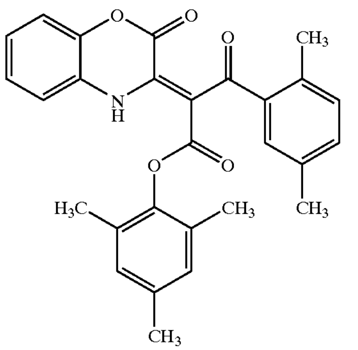 | 3-(2,5-Dimethyl-phenyl)-3-oxo-2-(2-oxo-4H-benzo[1,4]oxazin-3-ylidene)-propionic acid 2,4,6-trimethyl-phenyl ester |
| 8 | 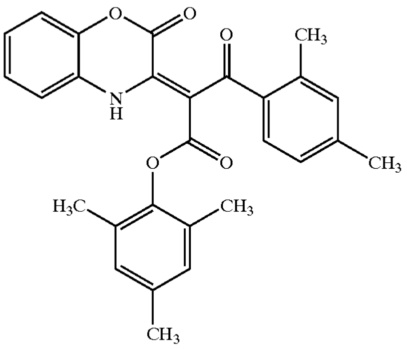 | 3-(2,4-Dimethyl-phenyl)-3-oxo-2-(2-oxo-4H-benzo[1,4]oxazin-3-ylidene)-propionic acid 2,4,6-trimethyl-phenyl ester |

-continued

| # | Structure | Name |
|---|---|---|
| 9 | 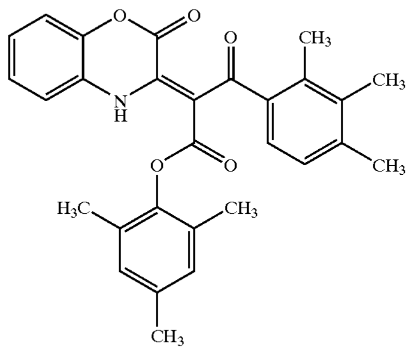 | 3-(3,4-Dimethyl-phenyl)-3-oxo-2-(2-oxo-4H-benzo[1,4]oxazin-3-ylidene)-propionic acid 2,4,6-trimethyl-phenyl ester |
| 10 | 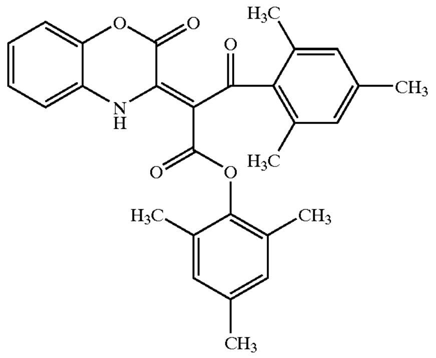 | 3-Oxo-2-(2-oxo-4H-benzo[1,4]oxazin-3-ylidene)-3-(2,4,6-trimethyl-phenyl)-propionic acid 2,4,6-trimethyl-phenyl ester |
| 11 | 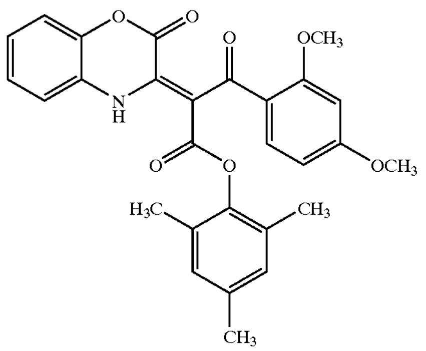 | 3-(2,4-Dimethoxy-phenyl)-3-oxo-2-(2-oxo-4H-benzo[1,4]oxazin-3-ylidene)-propionic acid 2,4,6-trimethyl-phenyl ester |
| 12 | 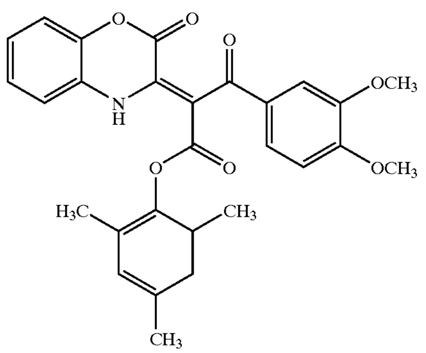 | 3-(3,4-Dimethoxy-phenyl)-3-oxo-2-(2-oxo-4H-benzo[1,4]oxazin-3-ylidene)-propionic acid 2,4,6-trimethyl-phenyl ester |

-continued

| # | Structure | Name |
|---|---|---|
| 13 | 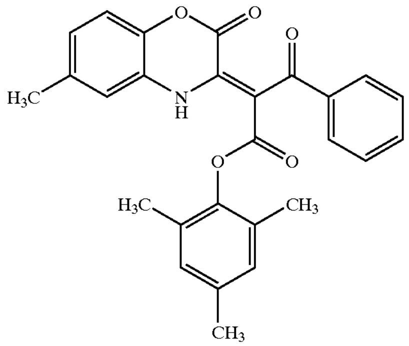 | 2-(6-Methyl-2-oxo-4H-benzo[1,4]oxazin-3-ylidene)-3-oxo-3-phenyl-propionic acid 2,4,6-trimethyl-phenyl ester |
| 14 | 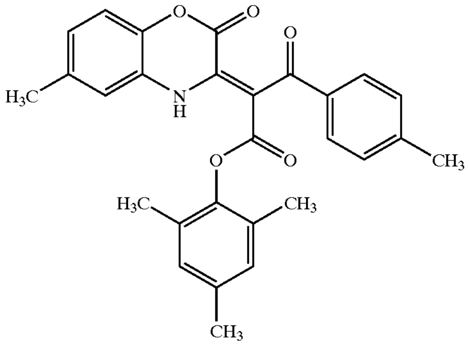 | 2-(6-Methyl-2-oxo-4H-benzo[1,4]oxazin-3-ylidene)-3-oxo-3-p-tolyl-propionic acid 2,4,6-trimethyl-phenyl ester |
| 15 | 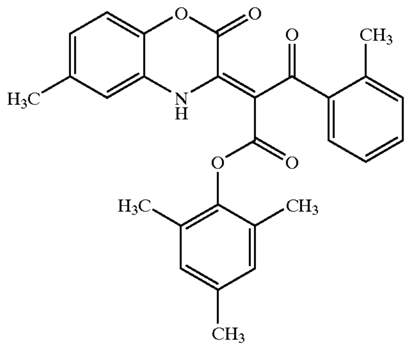 | 2-(6-Methyl-2-oxo-4H-benzo[1,4]oxazin-3-ylidene)-3-oxo-3-o-tolyl-propionic acid 2,4,6-trimethyl-phenyl ester |
| 16 | 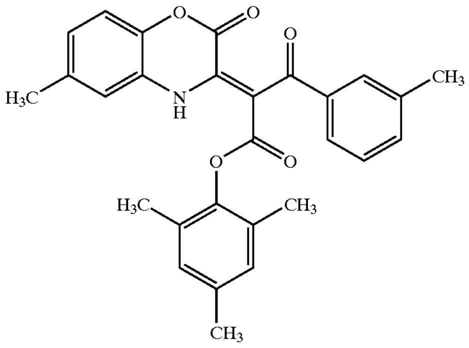 | 2-(6-Methyl-2-oxo-4H-benzo[1,4]oxazin-3-ylidene)-3-oxo-3-m-tolyl-propionic acid 2,4,6-trimethyl-phenyl ester |

-continued

| # | Structure | Name |
|---|---|---|
| 17 | 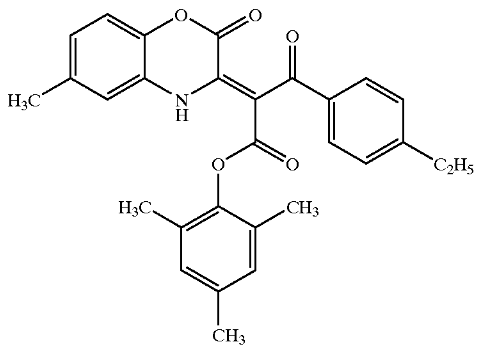 | 3-(4-Ethyl-phenyl)-2-(6-methyl-2-oxo-4H-benzo[1,4]oxazin-3-ylidene)-3-oxo-propionic acid 2,4,6-trimethyl-phenyl ester |
| 18 | 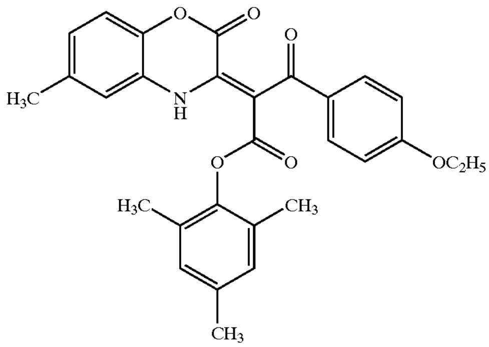 | 3-(4-Ethoxy-phenyl)-2-(6-methyl-2-oxo-4H-benzo[1,4]oxazin-3-ylidene)-3-oxo-propionic acid 2,4,6-trimethyl-phenyl ester |
| 19 | 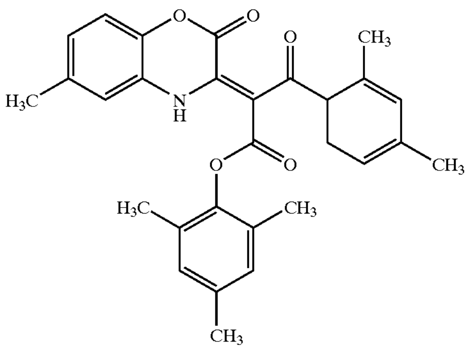 | 3-(2,4-Dimethyl-phenyl)-2-(6-methyl-2-oxo-4H-benzo[1,4]oxazin-3-ylidene)-3-oxo-propionic acid 2,4,6-trimethyl-phenyl ester |
| 20 | 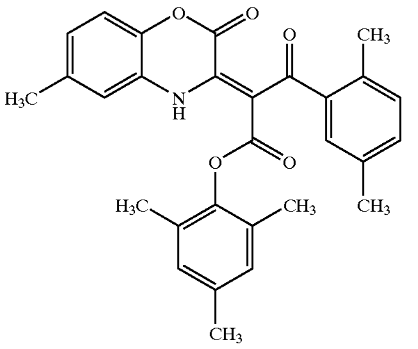 | 3-(2,5-Dimethyl-phenyl)-2-(6-methyl-2-oxo-4H-benzo[1,4]oxazin-3-ylidene)-3-oxo-propionic acid 2,4,6-trimethyl-phenyl ester |

-continued

| # | Structure | Name |
|---|---|---|
| 21 | 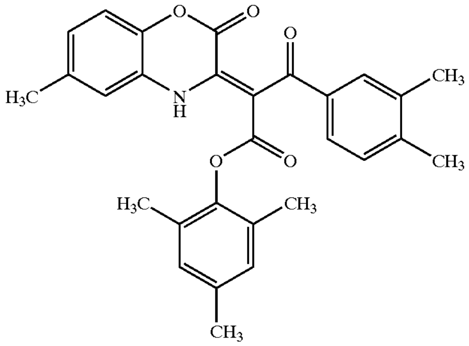 | 3-(3,4-Dimethyl-phenyl)-2-(6-methyl-2-oxo-4H-benzo[1,4]oxazin-3-ylidene)-3-oxo-propionic acid 2,4,6-trimethyl-phenyl ester |
| 22 | 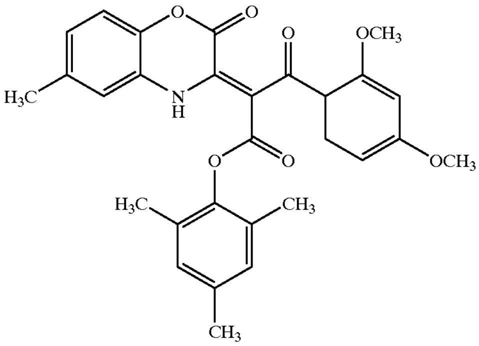 | 3-(2,4-Dimethoxy-phenyl)-2-(6-methyl-2-oxo-4H-benzo[1,4]oxazin-3-ylidene)-3-oxo-propionic acid 2,4,6-trimethyl-phenyl ester |
| 23 | 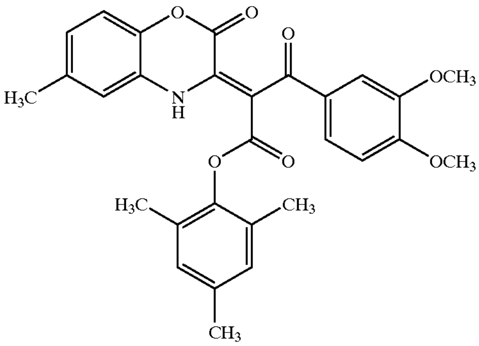 | 3-(3,4-Dimethoxy-phenyl)-2-(6-methyl-2-oxo-4H-benzo[1,4]oxazin-3-ylidene)-3-oxo-propionic acid 2,4,6-trimethyl-phenyl ester |
| 24 | 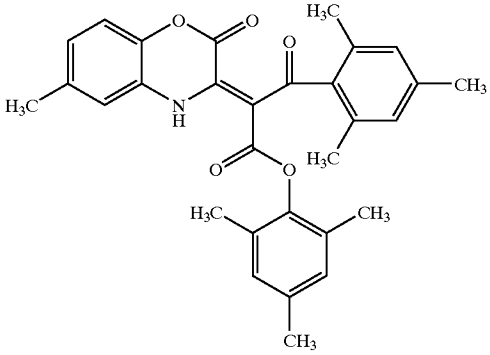 | 2-(6-Methyl-2-oxo-4H-benzo[1,4]oxazin-3-ylidene)-3-oxo-3-(2,4,6-trimethyl-phenyl)-propionic acid 2,4,6-trimethyl-phenyl ester |

The invention thus provides a method for the treatment and/or prophylaxis of *Mycobacteria tuberculosis* and related mycobacteria in humans or non-humans. This invention comprises administering an effective, non-toxic, amount of a heterocyclic compound according to the invention or a tautomeric form thereof and/or a pharmaceutically acceptable salt thereof and/or a pharmaceutically acceptable solvate thereof, to a tubercular(or mycobacteria infected) human or non-human in need thereof.

For human use, the compounds of the invention can be administered alone or jointly, but will generally be administered in a mixture with a pharmaceutical carrier selected with regard to the intended route of administration and standard pharmaceutical practice. For example, they may be administered orally, buccally or sublingually, in the form of tablets containing excipients such as starch or lactose, or in capasules or ovules either alone or in admixture with excipients, or in the form of elixirs or suspensions containing flavouring or colouring agents. The compounds may also be injected parenterally, for example intraveneously, intramuscularly, subcutaneously or intracoronarily. For parenteral administration, they are best used in the form of a sterile aqueous solution which may contain other substances, for example enough salts or glucose to make the solution isotonic.

For administration to man in the curative or prophylactic treatment of tuberculosis (or other mycobacterium), in vitro dosages of compounds of the invention will generally be in the range of from 5 to 500 mg daily for an average adult patient (70 kg). Thus for a typical adult patient, individual tablets or capsules contain from 2–500 mg of active compound, in a suitable pharmaceutically acceptable vehicle or carrier, for administration in single or multiple doses, once or several times per day. Dosages for intraveneous, buccal or sublingual administration will typically be within the range of from 5–1000 mg per single dose as required. In practice the physician will determine the actual dosing regimen which will be most suitable for an individual patient and it will vary with age, weight and response of the particular patient. The above dosages are exemplary of the average case but there can be individual instances in which higher or lower dosage ranges may be merited, and such are within the scope of this invention. The maximum non-toxic one time administration dose for the compound(s) of the invention appear to be 1000 mg/kg.

For human use, the compounds of the invention can be administered alone or jointly, but will generally be administered in admixture with a pharmaceutical carrier selected with regard to the intended route of administration and standard pharmaceutical practice. For example, they may be administered orally, buccally or sublingually, in the form of tablets containing excipients such as starch or lactose, or in capsules or ovules either alone or in admixture with excipients, on in the form of elixirs or suspensions containing flavouring or colouring agents. The compounds may also be injected parenterally, for example intraveneously, intramuscularly, subcutaneously or intracoronarily. For parenteral administration, they are best used in the form of a sterile aqueous solution which may contain other substances, for example enough salts or glucose to make the solution isotonic with blood.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A class of heterocyclics having the property of bacteriostatic agent activity against mycobacteria comprising 2-oxo-1,4-benzoxazine heterocyclics having the structural formula indicated by:

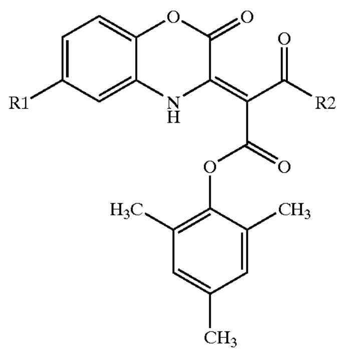

R1=H or $CH_3$

R2=aryl.

2. The heterocyclic according to claim 1, which is 4-benzoyl-3-benzoyloxy-2-(2-oxo-2H-1,2-benzoxazin-3-yl) pyrido[2,1-c][1,4]benzoxazin-1,5-dione.

3. The compound according to claim 1, which is 2,4,6-trimethylphenyl 2-(3,4-dihydro-2-oxo-2H-1,4-benzoxazin-3-ylidene)3-p-methoxyphenyl-3-oxo-propanoate.

4. A pharmaceutical composition comprising a non-toxic amount of the compound according to claim 1, or a tautomeric form thereof or a pharmaceutically acceptable salt thereof or pharmaceutically acceptable solvate thereof, and a pharmaceutically acceptable carrier therefore.

5. A method for the treatment of *Mycobacterium tuberculosis* (and other mycobacteria) in a human or non-human which comprises administering an effective, non-toxic amount of a compound according to claim 1, or a tautomeric form thereof and/or pharmaceutically acceptable salt thereof and/or a pharmaceutically acceptable solvate thereof, to a tubercular human or non-human in need thereof.

6. A method for the treatment of *Mycobacterium tuberculosis* and other mycobacteria in a human or non-human which includes administering to said human or non-human in need thereof, an effective, non-toxic amount of a compound according to claim 1, or a tautomeric form thereof and/or pharmaceutically acceptable salt thereof and/or a pharmaceutically acceptable solvate thereof which compound is 4-benzoyl-3-benzoyloxy-2-(2-oxo-2H-1,4-benzoxazin-3-yl)pyrido[2,1-c][1,4]benzoxazin-1,5-dione.

7. A method for the treatment of *Mycobacterium tuberculosis* in a human or non-human which includes administering to said human or non-human in need thereof, an effective, non-toxic amount of a compound according to claim 1, or a tautomeric form thereof and/or pharmaceutically acceptable salt thereof and/or a pharmaceutically acceptable solvate thereof which compound is 2.4.6-trimethylphenyl 2-(3,4-dihydro-2-oxo-2H-1,4-benzoxazine-3-ylidene)-3-p-methoxyphenyl-3-oxo-propanoate.

* * * * *